(12) United States Patent
Stonis et al.

(10) Patent No.: US 11,331,281 B2
(45) Date of Patent: May 17, 2022

(54) MIXTURE OF STABILIZED BIOLOGICALLY AVAILABLE CURCUMIN FOR ORODISPERSIBLE FORMULATIONS, FORMULATIONS OF BIOLOGICALLY AVAILABLE CURCUMIN, AND AN ORODISPERSIBLE TABLET WITH BIOLOGICALLY AVAILABLE CURCUMIN, AND ITS APPLICATION

(71) Applicants: mcePharma s. r. o., Bilovec (CZ); IMCoPharma a. s., Bilovec (CZ)

(72) Inventors: Jan Stonis, Pusta Polom (CZ); Ivan Mikes, Ostrava Svinov (CZ); Andrea Dolezalova, Hermanice (CZ); Jarmila Kralova, Prague (CZ); Milan Jakubek, Rychvald (CZ); Pavel Martasek, Prague (CZ); Vladimir Kral, Prague (CZ)

( * ) Notice: Subject to any disclaimer, the term of this patent is extended or adjusted under 35 U.S.C. 154(b) by 0 days.

(21) Appl. No.: 15/972,532

(22) Filed: May 7, 2018

(65) Prior Publication Data

US 2018/0325842 A1    Nov. 15, 2018

(30) Foreign Application Priority Data

May 8, 2017 (CZ) .................... CZ2017-260

(51) Int. Cl.
*A61K 31/12*    (2006.01)
*A61P 35/00*    (2006.01)
(Continued)

(52) U.S. Cl.
CPC ............ *A61K 31/12* (2013.01); *A61K 9/0056* (2013.01); *A61K 9/2018* (2013.01);
(Continued)

(58) Field of Classification Search
CPC .. A61K 31/12; A61K 36/9066; A61K 9/0056; A61K 9/2018; A61K 9/2059; A61K 9/5123
See application file for complete search history.

(56) References Cited

U.S. PATENT DOCUMENTS

| 4,642,903 A | 2/1987 | Davies |
| 5,188,825 A | 2/1993 | Iles et al. |

(Continued)

FOREIGN PATENT DOCUMENTS

| CZ | 307916 B6 | 8/2019 |
| WO | WO9703674 | 2/1997 |
| WO | WO2016053903 | 4/2016 |

OTHER PUBLICATIONS

Lecithin [online] retrieved from:https://www.medicalnewstoday.com/articles/319260.php; 5 pages (Year: 2017).*

(Continued)

*Primary Examiner* — Ernst V Arnold
(74) *Attorney, Agent, or Firm* — Cionca IP Law P.C.; Marin Cionca (57) ABSTRACT

Mixture of stabilised biologically available curcumin for orodispersible formulations, formulations of biologically available curcumin and orodispersible tablet with biologically available curcumin and its application. An orodispersible tablet with biologically available curcumin contains particles of extract of rhizome of plant *Curcuma longa*, which contains, at least, 95% by weight of curcumin, grounded to size 100 to 250 nm in mixture with mannitol in weight ratio 1 to 3:1 (mannitol:curcumin). Orodispersible tablet also contains an orodispersible carrier, and curcumin 100% biologically available through oral mucosa.

11 Claims, 9 Drawing Sheets

(51) Int. Cl.
  *A61K 9/00*    (2006.01)
  *A61K 9/20*    (2006.01)
  *A61K 36/9066* (2006.01)
  *A61K 9/51*    (2006.01)

(52) U.S. Cl.
  CPC .......... *A61K 9/2059* (2013.01); *A61K 9/5123* (2013.01); *A61K 36/9066* (2013.01); *A61P 35/00* (2018.01)

(56) References Cited

U.S. PATENT DOCUMENTS

| | | | |
|---|---|---|---|
| 5,631,023 | A | 5/1997 | Kearney et al. |
| 5,827,541 | A | 10/1998 | Yarwood et al. |
| 5,976,577 | A | 11/1999 | Green et al. |
| 10,098,898 | B1* | 10/2018 | Sung ............... A61K 31/606 |
| 2006/0246132 | A1* | 11/2006 | Johannsson .......... A61K 9/2027 424/468 |
| 2007/0293581 | A1* | 12/2007 | Hill .................... A61K 31/137 514/649 |
| 2011/0190399 | A1* | 8/2011 | Kar ........................ A61P 1/16 514/679 |
| 2013/0274343 | A1* | 10/2013 | Deshpande ............ A61K 31/12 514/679 |
| 2016/0051492 | A1 | 2/2016 | Nathan et al. |

OTHER PUBLICATIONS

Piperine (Gorgani et al. Compreshensive reviews in food science and food safety 2017;16: p. 124) (Year: 2017).*
Mannitol [online] retrieved from: https://www.naturalpedia.com/mannitol-sources-health-risks.html; (Year: 2017).*
Dextrin [online] retrieved from: http://www.nutrientsreview.com/carbs/polysaccharides-dextrins.html; 2016; 3 pages. (Year: 2016).*
Ashwell et al. Nutrition Today 2015;50(3): 129-134. (Year: 2015).*
Song et al. (Molecules 2016;21 (1386): 16 pages) (Year: 2016).*
Madane et al. (Drug Delivery 2016;23(4):1326-1334) (Year: 2016).*
Vandita et al. (Mol Pharmaceutics 2012;9:3411-3421) (Year: 2012).*
Shoba et al. (Abstract of: Plant Med 1998;64(4):353-6) 2 pages (Year: 1998).*
Macuja et al. (Advances in Environmental Chemistry 2015, Article ID 243785, 8 pages). (Year: 2015).*
Priyadarsini, K.I., The Chemistry of Curcumin: From Extraction to Therapeutic Agent, Molecules;2014; 19:20091-20112). (Year: 2014).*
Pharmaceutical Technology [online] retrieved from: https://www.pharmtech.com/view/selecting-superdisintegrants-orally-disintegrating-tablet-formulations; (2006;2006(5);3 pages) (Year: 2006).*
Roy et al. (Asian Journal of Pharmaceutics 2016(Suppl);10(4):S688-S692; 6 pages) (Year: 2016).*
Antony et al. (Indian Journal of Pharmaceutical Sciences 2008;445-449; 5 pages) (Year: 2008).*

* cited by examiner

CERTIFICATE OF ANALYSIS

Curcuma Longa Extract 95% Curcumins(HPLC)

Batch No.: Cjh20160505  Manufacture Date: 20160505  Expiry Date: 20180504

| General Information | | | |
|---|---|---|---|
| Part Used | Root | Solvents Used | Water&Ethanol |
| Botanical Source | *Curcuma longa L.* | Country f'Origin | China |

| ITEMS | SPECIFICATION | METHOD | TEST RESULTS |
|---|---|---|---|
| Physical&Chemical Data | | | |
| Color | Yellow | Organoleptic | Conform |
| Odour | Characteristic Fine | Organoleptic | Conform |
| Appearance | Powder | Organoleptic | Conform |
| Analytica Quality | | | |
| Identification | Identical to *R.S* sample | HPTLC | Identical |
| Curcumins | ≥95.0% | HPLC | 97.03% |
| Sieve analysis | 100 % through 80 mesh | USP36 <786> | Conform |
| Loss on Drying | ≤0.5% | Eur.Ph.7.0 [2.8.17] | 0.40 % |
| Total Ash | ≤10.0 % | Eur.Ph.7.0 [2.4.16] | 0.05 % |
| Bulk density | 40~60 g/100mL | Eur.Ph.7.0 [2.9.34] | 48 g/100mL |
| Tap density | 60~90g/100mL | Eur.Ph.7.0 [2.9.34] | 75 g/100mL |
| Contaminants | | | |
| Lead (Pb) | ≤3.0 mg/kg | Eur.Ph.7.0 <2.2.58>ICP-MS | 0.0215 mg/kg |
| Arsenic (As) | ≤2.0 mg/kg | Eur.Ph.7.0 <2.2.58>ICP-MS | 0.0116 mg/kg |
| Cadmium (Cd) | ≤≤1.0 mg/kg | Eur.Ph.7.0<2.2.58>ICP-MS | 0.0104 mg/kg |
| Mercury (Hg) | 0.1 mg/kg | Eur.Ph.7.0<2.2.58>ICP-MS | 0.0478 mg/kg |
| Solvents Residue | Meet Eur.Ph.7.0 <5.4> | Eur.Ph 7.0<2.4.24> | Conform |
| Pesticides Residue | Meet USP Requirements | USP36 <561> | Conform |
| Microbiological | | | |
| Total Plate Count | ≤10000 cfu/g | USP36 <61> | 10 cfu/g |
| Yeast &Mold | ≤1000 cfu/g | USP36 <61> | 10 cfu/g |
| E.Coli. | Negative | USP36 <62> | Conform |
| Salmonella | Negative | USP36 <62> | Conform |
| General Status | | | |
| Non-Irradiation | ≤700 | EN13751:2002<PSL> | 368 |
| Packing&Storage | Packed in paper-drums and two plastic-bags inside. N.W:25kgs .I.D.35 xH5 1cm; | | |
| Shelf life | Store in a well-closed container Away from moisture,light, oxygen. 24 months under the conditions above and in its original packaging. | | |

Manufacturer   Shaanxi Jiahe Phytochem Co., Ltd. Xi'an, P.R. China.

| # | Curcumin | Average of relative intensity of green fluorescence in the cell nucleus | Percentile efficacy compared to curcumin of Embodiment 1B | Multiple efficacy compared to product A and B |
|---|---|---|---|---|
| 1 | Embodiment 1B | 22.74 | 100% | 13X |
| 2 | Embodiment 1A | 17.57 | 77% | 10X |
| 3 | Embodiment 2 | 22.69 | 100% | 13X |
| 4 | Product A | 2.33 | 10% | 1X |
| 5 | Product B | 1.93 | 8% | 1X |

Fig. 10

| # | Curcumin | Average of relative intensity of green fluorescence in the cell nucleus | Multiple improvement of cellular absorption compared to native curcumin | Relative percentage |
|---|---|---|---|---|
| 1 | Native curcumin | 1.14 | 1 | 5 % |
| 2 | A mixture of stabilized bioavailable curcumine (curcumin: mannitol 1:2) | 16.37 | 13 | 72 % |
| 3 | Formulation of bioavailable curcumin (curcumin: mannitol: lecithin: piperine 1: 2: 1.5: 0.001) | 20.92 | 17 | 92 % |
| 4 | Orodispersible tablet with bioavailable curcumin (composition as tablet 1 according to Embodiment 6) | 22.74 | 18 | 100 % |

| Curcumin | Intensity of fluorescence (Time 0) |
|---|---|
| Embodiment 2 | 18771.56 |
| Product A | 84.36 |
| Ratio | 222.52 X |
| Rounded down | 220 X |

Fig. 13

MIXTURE OF STABILIZED BIOLOGICALLY AVAILABLE CURCUMIN FOR ORODISPERSIBLE FORMULATIONS, FORMULATIONS OF BIOLOGICALLY AVAILABLE CURCUMIN, AND AN ORODISPERSIBLE TABLET WITH BIOLOGICALLY AVAILABLE CURCUMIN, AND ITS APPLICATION

CROSS REFERENCE TO RELATED APPLICATIONS

This disclosure claims the priority of Czech patent application No. PV 2017-260, filed on May 8, 2017, and the entire contents thereof are incorporated herein by reference.

FIELD OF APPLICATION

Orodispersible tablets containing highly biologically available curcumin as food additive.

STATE OF THE ART

Curcumin is a yellow dye isolated of curcuma alias Indian saffron, an extract coming from a rhizome of turmeric (*Curcuma longa*). Curcumin is the most biologically active component of curcuma and it has attracted a great attention because of many performed and finished scientific studies which indicate that it can have many healthy benefits. Curcumin has been a subject of intensive research for example due to its antitumour effects, for its prophylactic effects against diseases of affluence, for its prophylactic effects against development of both Alzheimer's and Parkinson's diseases, and last but not least for its antiinflammatory and analgesic effects.

The extract of curcuma is the extract of rhizome of plant *Curcuma longa*. This extract is expected to have many beneficial healthy effects on the cardiovascular system, immune system, performance of liver, digestion, activity of the nerve system, function of the respiratory system, condition of skin and course of inflammatory reactions. Curcumin is the most biologically active component of this extract.

Curcuma extract is commonly available in the form of tablets, hard capsules, soft gelatine capsules and as emulsion.

Many different formulations and procedures for preparation of orodispersible tablets and minitablets are known. These tablets are suitable to all the patients who have problems with tablets swallowing or who do not like it, both children and seniors. Orodispersible formulations represent an alternative for these customers and they improve the application comfort in using food additives. The orodispersible drug forms are also advantageous for patients suffering from nausea, vomiting and diarrhoea. As the active substance is applied using the orodispersible drug form, there is quicker absorption of the medicinal component which runs less through mouth mucosa but most active substance is absorbed in the pre-gastric part of the digestive tract, and this causes marked decrease of the first-pass effect of liver metabolism, and this results in marked rise of efficiency of the administered active substance and of its dose. With this mechanism, the drug form improves the clinical effect of some active substances through increasing their bioavailability and decreasing occurrence of side effects due to by-passing first-pass of the liver metabolism effect. Formulating orodispersible preparations is demanding for several various reasons. Above all, this drug form must break down very quickly in the oral cavity. Moreover, too early release of an active substance in the mouth can result in problems with their application because of unpleasant taste of the active substance. The selected drug form should be adequately porous, so that it would break down quickly, but on the other hand it must bear mechanic load during transportation, storing and application. It is familiar that porous structures are very sensitive on air moisture and thus, problems concerning stability in long-time storing can develop. And finally, an orodispersible drug form with required organoleptic and pharmacokinetic properties must also be produced in commercially meaningful and applicable quantities.

Various methods of preparation and production of orally dispersible formulations have been developed that provide for their quick breakdown in the oral cavity, these techniques involve for example spray drying, lyophilization and wet granulation.

The technique of spray drying involves spraying of solution of active substance, of additional substances or of a mixture of both in a chamber where high temperature is maintained. This approach is not suitable for processing of thermolabile active substances or additional substances. Moreover, spray drying is very expensive and for this process it is characterised by high loss of the final product.

Lyophilization is a technique to remove moisture or solvent from solution using decreased temperature and decreased pressure. Unfortunately, it losses efficiency under large production scale and it is also limited by high price of the equipment, it is timely demanding and process conditions are difficult to maintain. An example can be Zydis® Technique. Tablets prepared using this technique are very brittle and they must be transported, stored and applied in a special case—adapted form of classical blister. These formulations are treated in U.S. Pat. Nos. 4,642,903, 5,188,825, 5,631,023, 5,827,541 and 5,976,577.

Wet granulation is an agglomeration technique with which granulated powder of high strength can be acquired, it breaks down slowly and thus is not suitable for orodispersible drug forms. Use of solvents and added steps for drying which this technique required, can moreover result in changes of polymorphic and pseudopolymorphic form of an active and/or additional substance and its degradation.

One of the issues related to curcumin is its biological availability. Even under high doses of native curcumin, only very small quantity reaches circulation after oral administration because of its quick metabolic conversion both in liver and in intestinal wall. A human body very poorly absorbs curcumin administered separately and the body can process only a small share of the administered dose efficiently. Capsules containing soya lecithin (Meriva) are produced to increase efficiency and bioavailability, use of nanotechniques (Theracurcumin) and dilution in water using polyvinylpyrrolidone is investigated. This method has claimed up to 46 times increased absorption when compared with the standard mixture of curcumin. Common application of curcumin together with piperine, an extract of black pepper, is a very efficient option. Piperine in body is able to block digestive enzymes that process curcumin. Another option is a recommendation to raise curcumin solubility in the way that it is first diluted in boiling water for 10 minutes (Kurien, 2009). Other investigations have, however, concluded that curcumin degrades by action of temperature. Curcumin C3 reduct by Swanson has been used as tetrahydrocurcuminoids but they also have higher stability under usual physiological pH levels.

Curcumin C3 complex, by Sabinsa, described in the patent document WO97/03674, has been used for comparison with marking "B Product". This product consists of extract of curcuma with 95% by weight of curcumin, demethoxycurcumin and bisdementhoxycurcumin of 300 mg. The extract was mixed together with piperine 2 mg, celluose and magnesium stearate and they together are sealed in gelatine capsules.

Liftea curcumin has been used for comparison with marking "A Product". Liftea curcumin is a preparation of extract of curcuma (95% of curcuminoids by weight) of 157 mg with 300 mg of inuline in a gelatine capsule containing magnesium stearate (antisintering agent). For the sake of comparison we have determined the size of particles of curcuma extract as 2 to 15 µm for both products.

Documents WO 2016/053903 and US 2016/0051492 have described pharmaceutical composition containing micronized curcumin, for example with gummy base for chewing gum production or combined with additives to compact tablets, and the tablets can be orodispersible. A marked disadvantage of both the documents is the common formulation tablet substance which has no positive effect on absorption and bioavailability of the present micro-curcumin. If we compare formulations produced according to these documents with the C3 complex commercial product by Sabinsa (B Product), only approximately 4.5 multiple of bioavailability of micro-curcumin was reached, and efficiency with patients monitored has differed dramatically, with some patients the level of curcumin in blood serum has even been almost zero—thus curcumin has not been absorbed at all.

NATURE OF THE INVENTION

A system for orodispersible formulations containing biologically available curcumim has been developed that operated at 200 times higher biological availability and 220 times higher solubility of curcumim against native curcumim involved in common food additives.

A mixture of stabilised biologically available curcumin for orodispersible formulations has been formed that contains particles of extract of rhizome of plant *Curcuma longa* containing 95% by weight of curcumin ground in the dry way in mixture with mannitol in the 1:1 weight ratio or any excess of mannitol to size of particles 100 to 250 nm, at least.

Further formulation of biologically available curcumin increasing biological availability of a mixture of stabilised biologically available curcumin for orodispersible formulations by 20% has been formed that contains a mixture of stabilised biologically available curcumin in lipide in weight ratio 0.35 to 1.5:1 of lipide against curcumin under presence of piperin in weight ratio 0.0025 to 0.1:1 of piperin against curcumin.

Subsequently an orodispersible tablet with biologically available curcumin has been produced increasing biological availability of mixture of stabilised biologically available curcumin by 30% that contains formulation of biologically available curcumin in orodispersible carrier that contains 20 to 80% by weight of tapioca starch, 10 to 30% by weight of pulverized bamboo fibre and 1 to 20% by weight of acid hydrolysed dextrine. This system for orodispersible formulations containing biologically available curcumin increases bioavailability of curcumin little by little, and it has been tested against the whole orodispersible tablet which shows up to 100% bioavailability and 92% bioavailability formulations of biologically available curcumin and the 72% bioavailability of mixture of stabilised biologically available curcumin has been related to it.

This way 100% biological availability has been provided for curcumin extract through oral mucosa, it has 220 times better solubility and 200 times better absorption ability and, above all, proven biological absorption ability for human cells.

Orodispersible tablets (ODT) and minitablets (ODMT) allow absorbance of curcumin directly through oral mucosa and pre-gastric parts of the digestive tract, without necessary pass through the digestive tract. Tablets and minitablets are suitable for vegans and vegetarians and even for persons suffering from food allergy, they contain neither lactose nor gluten. After simple mixing of the components of orodispersible carrier with mixture of stabilised biologically available curcumin or formulation of biologically available curcumin into developed orodispersible tablet substance, direct compression of tablets and minitablets follows and thus no further granulation, other production step or additive are necessary. It is not necessary to wash down tablets or minitablets, it is enough to solve them in mouth. The process of producing tablets and minitablets is not time-consuming, it represents high yields of the product, and there is no change in the form of the active substance or its reduction in production.

It is advantageous to produce the mixture of stabilised biologically available curcumin for orodispersible formulations using dry jet grinding or pin grinding of curcumin extract in mannitol where the weight ratio curcumin against mannitol is 1:2.

It is advantageous if the mixture of stabilised biologically available curcumin contains particles of curcumin extract in size 110-180 nm.

Formulation of biologically available curcumin increases biological availability of mixture of stabilised biologically available curcumin for orodispersible formulations by 20% and it contains mixture of stabilised biologically available curcumin in lipide in weight ratio 0.35 to 1.5:1 of lipide against curcumin under presence piperine in weight ratio 0.0025 to 0.1:1 piperine against curcumin, and it is advantageous to use lecithin as lipide.

An orodispersible tablet with biologically available curcumin increases biological availability of mixture of stabilised biologically available curcumin by 30% and it contains formulation of biologically available curcumin in orodispersible carrier which contains 20 to 80% by weight of tapioca starch, 10 to 30% by weight of pulverized bamboo fibre and 1 to 20% by weight of acid hydrolysed dextrin.

Curcumin extract is processed using jet or pin grinding with very uniform resulting distribution of particles, medium size of particles is 170 nm and 115 nm for jet and pin grinding, respectively.

It was established that very quick reverse aggregation of nanoparticles occurs within grinding of curcumin alone. The particles cluster and form aggregates of size similar to native curcumin crystals. Other sugars cannot be used for these purposes as stabilisers that prevent reverse aggregation of ground curcumin. Most sugars are highly hygroscopic and thus they cannot be used in orodispersible tablets. Moreover, sugars work in curcumin formulation as substrates for possible microbial contamination. When grinding curcumin with glucose, aggregation of nanoparticles occurs because of high moisture level. Similarly aggregation of nanoparticles occurs when using sorbitol or xylitol. Moreover, these sugars stick because of air moisture and thus they complicate the production process. When using erythritol, large crystals form and they are unsuitable for bioavailable formulation of curcumin.

The ideal stabiliser for grinding of curcumin particles proved to be mannitol. Mixture of stabilised biologically available curcumin is prepared by common dry grinding of curcumin extract with manitol, namely in precise ratio at least 1:1 or with manitol excess. This ratio provides for stability of ground nano-curcumin when reverse aggregation of curcumin nanoparticles to larger units does not occur, which would result in decreasing bioavailability. It is advantageous to have the weight ratio mannitol:curcumin je 2:1, and also ratio 1 to 3:1 is functional. Further increase of mannitol content in the mixture has no effect on size and stabilisation of curcumin nanoparticles and it only dilutes the active substance content. It has been proven that moisture level has risen just by 0.5% after 3 month storing of stabilised nanocurcumin in mixture with mannitol in weight ratio 1:2. Also it has been shown that bioavailability of nanocurcumin without stabiliser cannot be determined in practice as it aggregates immediately without presence of a stabiliser, best if mannitol.

These parameters apply for jet grinding of native curcumin: particle size is in the interval from 130 to 250 nm. Curcumin is ground with stabiliser, it is advantageous with mannitol, it is advantageous in ratio 2:1 (mannitol:curcumin) in a dry way in a jet grinder. Feed pressure is 30 to 70 PSI, grinding pressure 30 to 70 PSI and the ground process is repeated twice. This the required medium size of particles and narrow distribution particles are achieved which provide for high bioavailability of curcumin.

These parameters apply for pin grinding of native curcumin: particle size is in the interval from 100 to 170 nm. Curcumin is ground with stabiliser, it is advantageous with mannitol, it is advantageous in the ratio 2:1 against curcumin in a dry way in a pin mill. Several types of rotors can be used for grinding, it is advantageous to use rotors OR PV, rotors OR PV with round tools of the type or rotors BR PV or rotors BR PV with controlled flow of material (or with slowing flow of material and its compaction in intermediate spaces which are combined with spreaders labelled 11 and 12. Feeding of material in the machine is manual or vibration. This way decreased size of particles and narrow distribution particles are achieved which provide for high bioavailability of curcumin.

We have established that ground curcumin with grain size 100 nm to 250 nm, advantageous if 110 to 180 nm, is up to 100% bioavailable and absorbable into an organism when compared with native curcumin (medium size of particles 2 to 15 µm). Formulation of biologically available curcumin is added to additive, orodispersible carrier which forms a resulting form of a tablet or a minitablet which is easily soluble in the mouth and it is mostly produced of natural raw materials. Formulation of biologically available curcumin contains piperin and lipid, it is advantageous if lecithin. Piperin blocks function of digestive enzymes, processing curcumin, and it increases its bioavailability indirectly. Lipid changes surface tension of cell membranes and it has a positive effect on bioavailability of curcumin and its penetration in cells. This way it facilitates absorption of curcumin in the tissue.

A mixture of ground curcumin, mannitol, piperine and lecithine, thus formulation of biologically available curcumin is mixed s tablet substance/orodispersible carrier which is composed of several components and which is prepared using the fluid granulation process. This method provides for generation of porous structure of granulated powder which breaks down quickly but, on the other hand, it is resilient enough to withstand transport of tablets. Within fluid granulation, filling agents (tapioca starch, bamboo fibre) are suspended in flow of heated air. The solution of a binding agent containing dextrine and Stevio-Rebauosid A, advantageous if isomalt or sorbitol, is applied into this way formed fluid bed. The purpose of the binding agent is to create physical link among the free particles of powder (starch, pulverized bamboo fibre) and finally to form a granulate. The granulate is dried while suspended and then it is advantageous to add sweetening agents (erythritol, sorbitol or xylitol) which keep pleasant feeling after being dissolved in the mouth and also it is advantageous to add pre-gelatinized starch, silicon dioxide and glyceryl dibehenate and then the mixture is mixed properly.

Is advantageous to use aroma or flavour, for example orange, peppermint, citrone, strawberry, banana, raspberry, sour cherry, cherry or other, for better feeling in the mouth after the tablet is administered.

After formulation of biologically available curcumin is added to orodispersible carrier, compact tablets and minitablets of any size can be compacted, they are packed wet into a tight shell, they can be packed in blisters separately. After release from a blister, tablets and minitablets are administered in the mouth and they break down within 35 seconds.

Bioavailability of curcumin in an orodispersible tablet has been compared against commercial preparation labelled as products A and B. Bioavailability and solubility have been tested through measurement of fluorescence of a tablet diluted in solution and after absorption in tumour cells—in vitro tests. Examples document that penetration of ground curcumin in cells has really occurred, namely up to 13 times more efficiently against commercial preparations where relative intensity of green fluorescence of curcumin in cell nucleus for products A and B is 2.33 and 1.93, respectively, while relative intensity of green fluorescence of curcumin in cell nucleus of biologically available curcumin according to the invention is 22.74. When calculated, bioavailability of products A and B is only 10% and 8%, respectively, against bioavailable curcumin in an orodispersible tablet according to the invention. The tests on solubility of biologically available curcumin have been carried out in PBS buffer and they have shown that the complete dissolution of tablets can occur within 30 seconds. Solubility has been measured through intensity of fluorescence and it has been for biologically available curcumin 220 times higher than for the A product.

Also formulations with native curcumin have been subjected to extensive tests, they have involved lactose, whey and other sugars but these formulations have not shown the optimum function in tests on biological availability and solubility under the required conditions. The optimum composition has shown to be tapioca starch (20 to 80% by weight), pulverized bamboo fibre (10 to 30% by weight), erythritol (10 to 50% by weight), pre-gelatinised starch (0.01 to 10% by weight), acid hydrolysed dextrine (1 to 20% by weight), silicon dioxide (0.5 to 4% by weight) and glyceryl dibehenate (0.4 to 4% by weight).

Also other slippy substances can function instead silicon dioxide and glyceryl dibehenate, e.g. magnesium stearate, aluminium stearate, sodium lauryl sulphate, talc, polyethylene glycol, stearic acid, boric acid, namely in concentration 1 to 8% by weight, best if 1 to 5% by weight. Aroma can be used in concentration 0.01 to 10% by weight.

Tablets weight 150 to 300 mg and their diameter is 7 to 12 mm. Minitablets weight 35 to 70 mg and their diameter is 4 to 6 mm. Minitablets have strength 5 to 100 N, best if 20 to 50 N and their abrasion is less than 1%.

Also a vast series of specimens of different size of particles ground curcumin extract has been tested, and the best solubility and bioavailability has been found in ground curcumin with the size 115 to 180 nm.

OVERVIEW OF DRAWINGS

EXAMPLES OF INVENTION EXECUTION

Example 1A

Processing of Initial Extract

Figure 1:
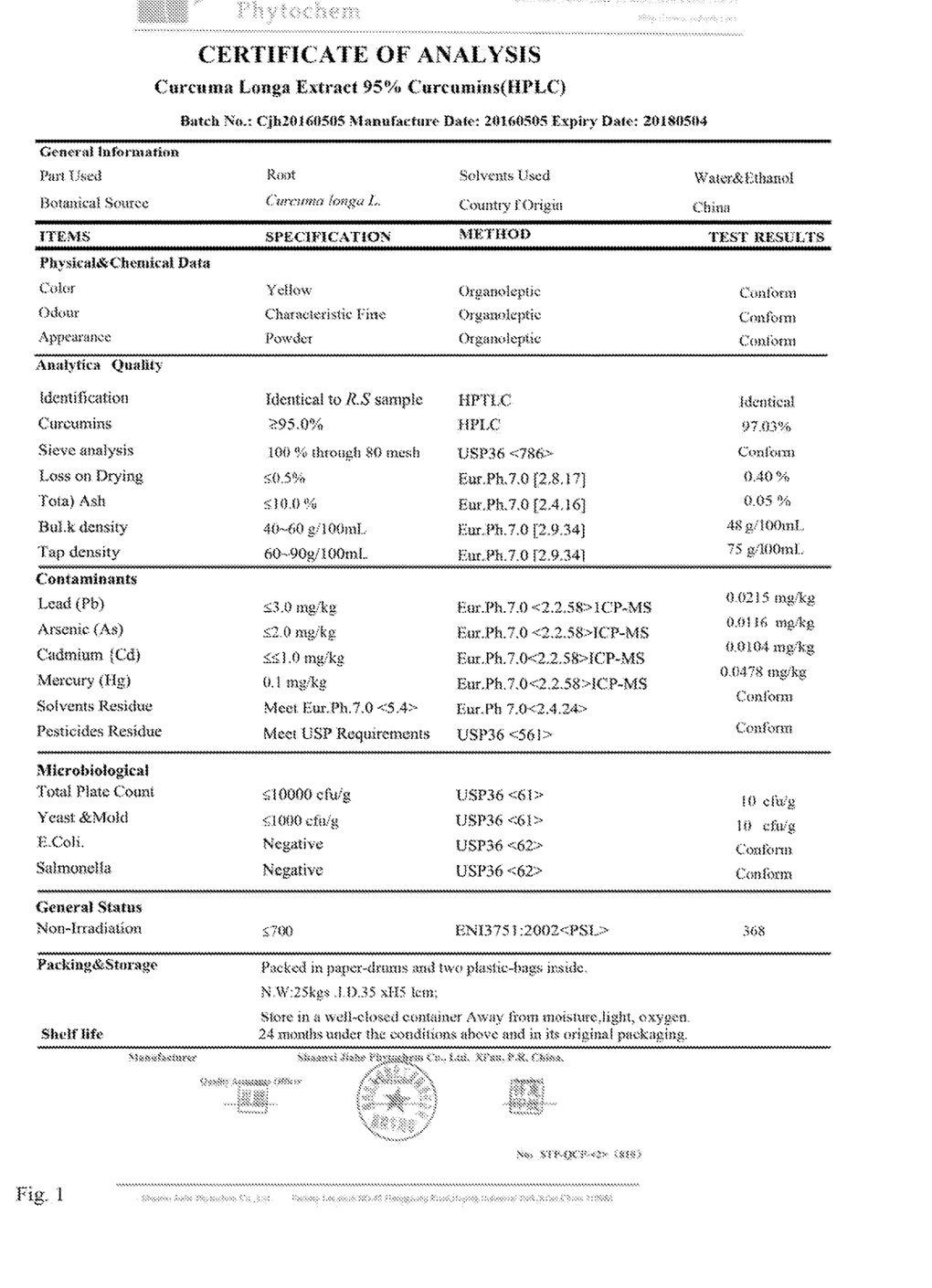
FIG. 1 Certificate of analysis of used curcumin extract

Curcuma of rhizome of plant *Curcuma longa* L. has been used as parent raw material for extraction. The extract has contained 97.03% by weight of curcumin and ash content has been 0.05% by weight. The full certificate for analysis of the used extract is presented in FIG. 1.

Figure 2:
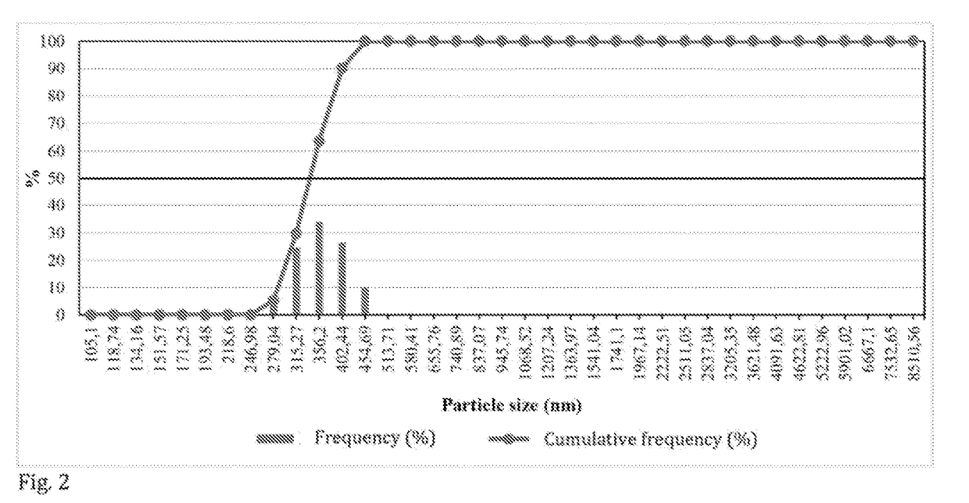
FIG. 2 Analysis of size of particles in specimen of curcumin extract prepared according to Example 1A ground by jet grinding (feed pressure=50 PSI, grinding pressure=70 PSI, once ground).

25 g of curcumin extract has been ground in a dry way in a laboratory jet mill together with mannitol in ratio 2:1 (mannitol against curcumin). The input feed pressure has been 70 PSI (344.738 kPa) and grinding pressure has been 50 PSI (482.633 kPa). The grinding process has run once for 96 minutes at 25° C. The resulting medium size of particles of ground curcumin has been measured using dynamic light dispersion and it has ranged around 335.735 nm. The detailed results of the ground extract analysis are in FIG. 2. This medium size of particles has been determined as unsuitable for use as a highly absorbable active substance.

Example 1B

Processing of Initial Extract—Preparation of Mixture of Stabilised Nanocurcumin

Curcuma with botanic name *Curcuma longa* L. has been used as the parent raw material for extraction. The extract has contained 97.03% by weight of curcumin and ash content has been 0.05% by weight. The full certificate for analysis of the used extract is presented in FIG. 1.

Figure 3:
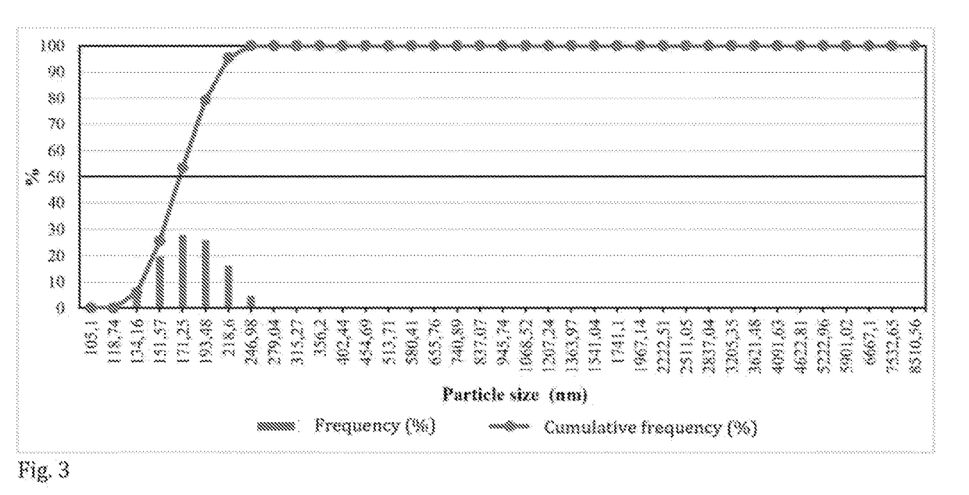
FIG. 3 Analysis of size of particles in specimen of curcumin extract prepared according to Example 1B ground by jet grinding (feed pressure=50 PSI, grinding pressure=50 PSI, twice ground).

250 g of curcumin extract has been ground in a dry way in a laboratory jet mill together with 500 g of mannitol, i.e. in ratio 1:2. The input feed pressure has been 50 PSI (482.633 kPa) and grinding pressure has been 50 PSI (482.633 kPa). The grinding process has run twice subsequently for 96 minutes at 25° C. The resulting medium size of particles of curcumin has been measured using dynamic light dispersion and it has been determined as 171.17 nm which has been the smallest achieved medium size of particles; distribution of particles has been (134.16 to 246.98 nm). The detailed results of the ground extract analysis are in FIG. 3. This medium size of particles has been determined as suitable for use as a highly absorbable active substance.

Example 2

Processing of Initial Extract—Preparation of Mixture of Stabilised Nanocurcumin

Curcuma with botanic name *Curcuma longa* L. has been used as the parent raw material for extraction. The extract has contained 97.03% by weight of curcumin and ash content has been 0.05% by weight. The full certificate for analysis of the used extract is presented in FIG. 1.

300 g of curcumin extract has been ground in a dry way in a laboratory pin mill together with 600 g of mannitol, i.e.

in ratio 1:2. The OR PV rotor with round tools has been used as the rotor, combined with spreader 11.

Figure 4:
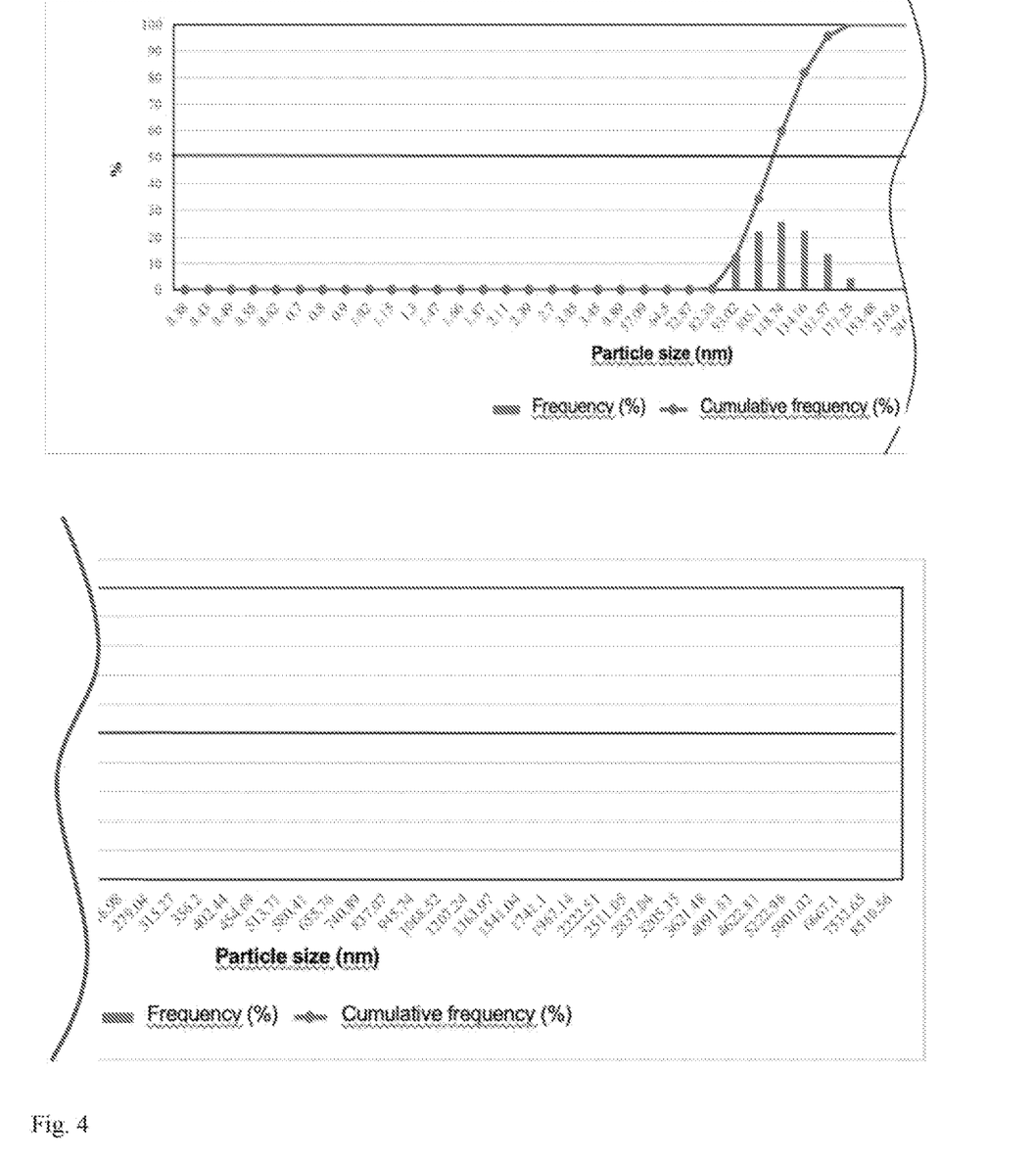
FIG. 4 Analysis of size of particles in specimen of curcumin extract prepared according to Example 2 ground using pin grinding.

The resulting medium size of particles of curcumin has been measured using dynamic light dispersion and it has been determined as 115.5 nm which has been the smallest achieved medium size of particles; distribution of particles has been (100.02-171.25 nm). The detailed results of the ground extract analysis are presented in FIG. 4. This medium size of particles has been determined as suitable for use as a highly absorbable active substance.

Example 3

Preparation of Tablet Substance/Excipient

Tablet substance, in the function of a carrier matrix tablet and a minitablet, without active substances, have been prepared in a fluid granulation process. Within the fluid granulation, 713.294 g of tapioca starch and 124.802 g of pulverized bamboo fibre has been suspended in flow of air heated to 80 to 90° C. Little by little a solution has been applied in the created fluid bed. The solution has been generated by dilution of 14.799 g of LyckebyPlus 1200H and 0.636 g of Stevia-Rebausiode A in hot water. After application of the solution, the generated granulate has been dried suspended, till it has contained 4 to 8% by weight of residual moisture. Subsequently, 125.246 g of erythritol, 8.350 g of pre-gelatinised starch, 8.583 g of silicon dioxide and 4.291 g of glyceryl dibehenate has been added to the granulate. Subsequently, the resulting mixture has been mixed properly in a simple planetary mixer for 5 minutes.

Process Parameters of Fluid Granulation:

| Fluid granulation stage | Time (min) | Valve Capacity (%) | Inlet temperature (° C.) | Outlet temperature (° C.) | Temperature of product (° C.) |
| --- | --- | --- | --- | --- | --- |
| Device preheating | $T_0$-$T_{10}$ | 15-25 | 20-100 | 16-35 | 16-40 |
| Granulation-application of binding agent | $T_{10}$-$T_{30}$ | 15-35 | 70-100 | 30-40 | 25-35 |
| Granulate drying | $T_{30}$-$T_{50}$ | 25-35 | 45-80 | 30-35 | 30-40 |

Example 4

Example 4A

Preparation of Tablet Substance/Excipient

Tablet substance, in the function of a carrier matrix tablet and a minitablet, without active substances, have been prepared in a fluid granulation process. Within the fluid granulation, 692.562 g of tapioca starch and 221.525 g of pulverized bamboo fibre has been suspended in flow of heated air. Little by little a solution has been applied in the created fluid bed. The solution has been generated by dilution 15.845 g of Lyckeby plus 1200H and 0.883 g of Stevio-rebauoside A in hot water. After application of the solution, the generated granulate has been dried suspended, till it has contained 4-8% by weight of residual moisture. Subsequently, 225.699 g of erythritol, 22.598 g of pre-gelatinised starch, 15.223 g of silicon dioxide and 30.615 g of glyceryl dibehenate has been added to the granulate. Subsequently, the resulting mixture has been mixed properly.

Example 4B

Preparation of Tablet Substance/Excipient

Tablet substance, in the function of a carrier matrix tablet and a minitablet, without active substances, have been prepared in a fluid granulation process. Within the fluid granulation, 559.512 g of tapioca starch and 215.525 g of pulverized bamboo fibre has been suspended in flow of heated air. Little by little a solution has been applied in the created fluid bed. The solution has been generated by dilution of 16.799 g of isomalt and 0.883 g of Steviorebauoside A in hot water. After application of the solution, the generated granulate has been dried suspended, till it has contained 4 to 8% by weight of residual moisture. Subsequently, 130.699 g of erythritol, 43.250 g of pre-gelatinised starch, 17.645 g of silicon dioxide and 170.645 g of glyceryl dibehenate has been added to the granulate. Subsequently, the resulting mixture has been mixed properly.

Example 4C

Preparation of Tablet Substance/Excipient

Tablet substance, in the function of a carrier matrix tablet and a minitablet, without active substances, have been prepared in a fluid granulation process. Within the fluid granulation, 706.512 g of tapioca starch and 240.802 g of pulverized bamboo fibre has been suspended in flow of heated air. Little by little a solution has been applied in the created fluid bed. The solution has been generated by dilution of 13.845 g of sorbitol (NeoSorb) and 0.883 g of Stevio-rebauoside A in hot water. After application of the solution, the generated granulate has been dried suspended, till it has contained 4 to 8% by weight of residual moisture. Subsequently, 133.204 g of erythritol, 36.725 g of pre-gelatinised starch, 17.082 g of silicon dioxide and 21.341 g of glyceryl dibehenate has been added to the granulate. Subsequently, the resulting mixture has been mixed properly.

Example 5

Production of a Minitablets 1

To 400 g of tablet substance prepared according to Example 4A, the substances as follows have been added: 60 g of mixture of stabilised nanocurcumin prepared according to Example 2, i.e. 20 g of ground curcumin and 40 g of mannitol, 30 g of lecithin, 0.2 g of piperine and 6.67 g of orange aroma. All these components have been homogenised and compacted using direct pressing and this way compact, porous tablets, have been produced, weighting 50 mg.

Production of Minitablets 2

To 400 g of tablet substance prepared according to Example 3, the substances as follows have been added: 60 g of mixture of stabilised nanocurcumin prepared according to Example 1B, i.e. 20 g of ground curcumin and 40 g of mannitol, 30 g of lecithin, 0.2 g of piperine and 6.67 g of peppermint aroma. All these components have been homogenised and compacted using direct pressing and this way compact, porous tablets, have been produced, weighting 50 mg.

Production of Minitablets 3

To 223 g of tablet substance prepared according to Example 4B, the substances as follows have been added: 160 g of mixture of stabilised nanocurcumin prepared according to Example 1B with ratio mannitol:curcumin 1:1, i.e. 80 g of ground curcumin and 80 g of mannitol, 30 g of lecithin, 0.2 g of piperine and 6.67 g of orange aroma. All these components have been homogenised and compacted using direct pressing and this way compact, porous tablets, have been produced, weighting 50 mg.

Production of Minitablets 4

To 223 g of tablet substance prepared according to Example 3, the substances as follows have been added: 160 g of mixture of stabilised nanocurcumin prepared according to Example 2 with ratio mannitol:curcumin 1:1, i.e. 80 g of ground curcumin and 80 g of mannitol, 30 g of lecithin, 0.2 g of piperine and 6.67 g of peppermint aroma. All these components have been homogenised and compacted using direct pressing and this way compact, porous tablets, have been produced, weighting 50 mg.

Production of Minitablets 5

To 400 g of tablet substance prepared according to Example 4C, the substances as follows have been added: 60 g of mixture of stabilised nanocurcumin prepared according to Example 2, i.e. 20 g of ground curcumin and 40 g of mannitol, 30 g of sunflower lecithin and 0.17 g of piperine. All these components have been homogenised and compacted using direct pressing and this way compact, porous tablets, have been produced, weighting 50 mg.

Production of Minitablets 6

To 409 g of tablet substance prepared according to Example 3, the substances as follows have been added: 60 g of mixture of stabilised nanocurcumin prepared according to Example 1A, i.e. 20 g of ground curcumin and 40 g of mannitol, 20 g of sunflower lecithin and 0.17 g of piperine. All these components have been homogenised and compacted using direct pressing and this way compact, porous tablets, have been produced, weighting 50 mg.

Example 6

Production of tablets 1

To 1903 g of tablet substance prepared according to Example 3, the substances as follows have been added: 60 g of mixture of stabilised nanocurcumin prepared according to Example 2, i.e. 20 g of ground curcumin and 40 g of mannitol, 30 g of lecithin, 0.2 g of piperine and 6.67 g of orange aroma. All these components have been homogenised and compacted using direct pressing and this way compact, porous tablets, have been produced, weighting 150 mg.

Production of Tablets 2

To 1903 g of tablet substance prepared according to Example 4A, the substances as follows have been added: 60 g of mixture of stabilised nanocurcumin prepared according to Example 1B, i.e. 20 g of ground curcumin and 40 g of mannitol, 30 g of lecithin, 0.2 g of piperine and 6.67 g of peppermint aroma. All these components have been homogenised and compacted using direct pressing and this way compact, porous tablets, have been produced, weighting 200 mg.

Production of Tablets 3

To 1633 g of tablet substance prepared according to Example 3, the substances as follows have been added: 24 g of mixture of stabilised nanocurcumin prepared according to Example 2, i.e. 8 g of ground curcumin a 16 g of mannitol, 12 g of lecithin, 0.8 g of piperine and 6.67 g of orange aroma. All these components have been homogenised and compacted using direct pressing and this way compact, porous tablets, have been produced, weighting 200 mg.

Production of Tablets 4

To 1633 g of tablet substance prepared according to Example 4C, the substances as follows have been added: 24 g of mixture of stabilised nanocurcumin prepared according to Example 1B, i.e. 8 g of ground curcumin and 16 g of mannitol, 12 g of lecithin, 0.8 g of piperine and 6.67 g of peppermint aroma. All these components have been homogenised and compacted using direct pressing and this way compact, porous tablets, have been produced, weighting 200 mg.

Production of Tablets 5

To 1423 g of tablet substance prepared according to Example 3, the substances as follows have been added: 45 g of mixture of stabilised nanocurcumin prepared according to Example 1B, i.e. 15 g of ground curcumin and 30 g of mannitol, 12 g of lecithin, 0.8 g of piperine and 6.67 g of orange aroma. All these components have been homogenised and compacted using direct pressing and this way compact, porous tablets, have been produced, weighting 300 mg.

Production of Tablets 6

To 1423 g of tablet substance prepared according to Example 4B, the substances as follows have been added: 45 g of mixture of stabilised nanocurcumin prepared according to Example 2, i.e. 15 g of ground curcumin and 30 g of mannitol, 12 g of lecithin, 0.8 g of piperine and 6.67 g of peppermint aroma. All these components have been homogenised and compacted using direct pressing and this way compact, porous tablets, have been produced, weighting 150 mg.

Production of Tablets 7

To 1250 g of tablet substance prepared according to Example 3, the substances as follows have been added: 500 g of mixture of stabilised nanocurcumin prepared according to Example 1B, i.e. 167 g of ground curcumin and 333 g of mannitol, 250 g of sunflower lecithin and 0.16 g of piperine. All these components have been homogenised and compacted using direct pressing and this way compact, porous tablets, have been produced, weighting 200 mg.

Production of Tablets 8

To 1250 g of tablet substance prepared according to Example 4B, the substances as follows have been added: 500 g of mixture of stabilised nanocurcumin prepared according to Example 2, i.e. 167 g of ground curcumin and 333 g of mannitol, 250 g of sunflower lecithin and 0.16 g of piperine. All these components have been homogenised and compacted using direct pressing and this way compact, porous tablets, have been produced, weighting 300 mg.

Production of Tablets 9

To 951.5 g of tablet substance prepared according to Example 4A, the substances as follows have been added: 60 g of mixture of stabilised nanocurcumin prepared according to Example 1B, i.e. 20 g of ground curcumin and 40 g of mannitol, 30 g of sunflower lecithin, 0.2 g of piperine and 6.67 g of orange aroma. All these components have been homogenised and compacted using direct pressing and this way compact, porous tablets, have been produced, weighting 100 mg.

Production of Tablets 10

To 951.5 g of tablet substance prepared according to Example 4A, the substances as follows have been added: 60 g of mixture of stabilised nanocurcumin prepared according to Example 1B, i.e. 20 g of ground curcumin and 40 g of mannitol, 30 g of sunflower lecithin, 0.2 g of piperine and 6.67 g of peppermint aroma. All these components have been homogenised and compacted using direct pressing and this way compact, porous tablets, have been produced, weighting 100 mg.

Example 7

Experiments on Bioavailability (Absorption Ability)—Tumour Cells In Vitro

Figure 5:
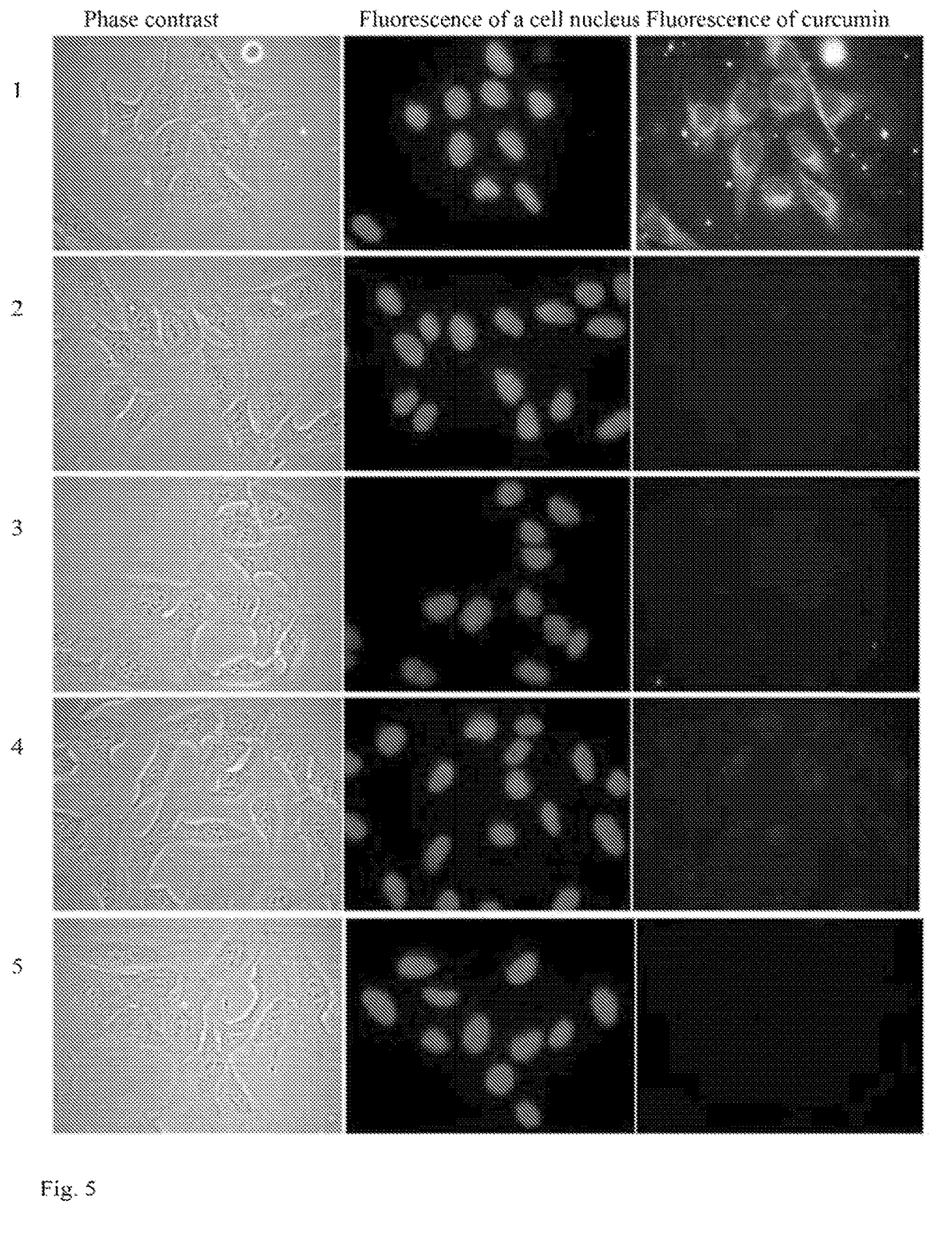
FIG. 5 Snaps by fluorescence inversion microscope Leica DM IRB of phase contrast, of fluorescence-coloured nucleus and fluorescence of curcumin, 1—ground curcumin according to Example 1B, 2—native curcumin micronized in composition like tablet 1 according to Example 6, 3—native curcumin micronized with tablet substance according to Example 4A (that means without lecithin and piperine), 4—native curcumin micronized with mannitol, lecithin and piperine, 5—native curcumin mikornizovaný with mannitol for cell line U-2, human osteosarcoma.

Several types of curcumin formulation have been prepared:
1—bioavailable curcumin according to Example 1B,
2—native curcumin micronized in composition like tablet 1 according to Example 6,
3—native curcumin micronized with tablet substance according to Example 4A (that means without lecithin and piperine),
4—native curcumin micronized with mannitol, lecithin and piperine,
5—native curcumin micronized with mannitol Formulations of curcumin (4 mg) have been resuspended in 1 ml of PBS (buffer saline solution), sound treated in the bath for 5 minutes and 40 µl of this suspension has been added into 2 ml of a cultural medium to the cells (cell line U-2 OS, human osteosarcoma; cell line MCF-7, human breast carcinoma). Incubation with cells has run in an incubator at 37° C. for 1 hour, and then reference dye Hoechst 33342 has been added in the medium for 15 minutes (resulting concentration 0.5 µM) which marks cell nuclei with fluorescence. The cells have been rinsed with the medium without phenol red, they have been viewed using a fluorescence inversion microscope Leica DM IRB using an oil immersion objective (×63) and scanned with a camera DFC 480. The same cell field has been scanned using common light (phase contrast), and fluorescence cubes Leica A (excitation filter BP340-380 and long pass filter LP 425 for emission) showing blue fluorescence Hoechst 33342 and Leica 13 (excitation filter BP 450-490 and long-pass filter LP 515 for emission) showing green fluorescence of curcumin. All the tested variants of curcumin have been scanned with a camera with the same setting to allow their comparison. The snaps are presented in FIGS. 5 and 6. In vitro experiments have confirmed penetration of the prepared formulation into the cell system.

Quantitative determination of curcumin in cell through measurement of fluorescence cell lysates and fluorescence microscopy A reliable and sensitive method for fluorescence determination of curcumin has been developed.

The method is based on quantification of fluorescence substance curcumin. The methodology has been used to determine efficiency of intracelular transport of curcumin formulations where the results have been compared with native and micronized curcumin where we have observed very low intracelular absorption while some among the tested formulations have provided high values of intracelular fluorescence and these have been assessed quantitatively. Within our approach, curcumin in cell can be quantified directly or in cell lysates without necessary pre-cleaning of a sample. The assessment of fluorescence intensity has been performed using image analysis and software processing of the image of cells from a microscope where the ration of relative intensity of green fluorescence in the samples has been measured.

According to the best penetration of curcumin into a cell system, curcumin prepared according to Example 1B has been selected as the optimum bioavailable one.

Example 8

Figure 10:
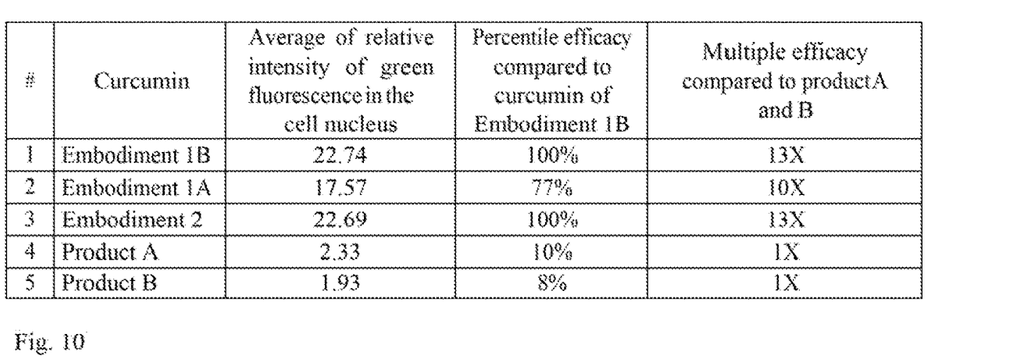
FIG. 10 Table for determination of intensity of fluorescence of the curcumin specimen from snaps FIG. 7.

Comparison of Solubility of an Orodispersible Tablet Containing Highly Bioavailable Curcumin with Commercial Product A and B Tablet 1 prepared according to Example 6 and tablets of products A and B (4 mg of curcumin) have been resuspended in 1 ml of water under continuous stirring with a magnetic mixer at 37° C. Intensity of fluorescence as dependent on time has been assessed for 1 hour. Increase of fluorescence in the solution has marked dissolution of the tablet and release of curcumin. The fluorescence maxima and this full dissolution of the tablet is documented in graph in FIG. 10. For formulation of curcumin according to this invention, 220× better solubility against commercial native form of curcumin has been achieved.

Example 9

Figure 6:
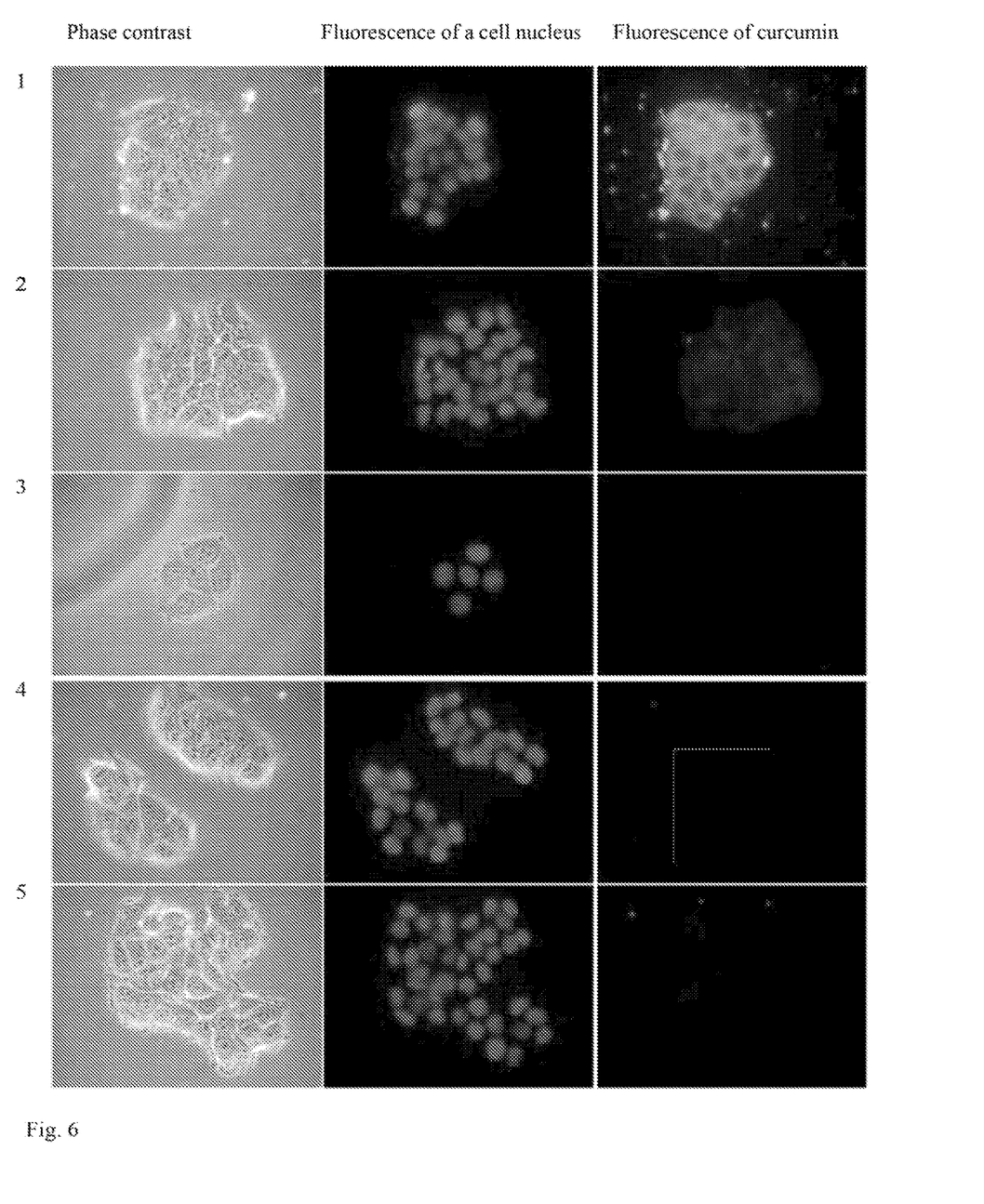
FIG. 6 Snaps by fluorescence inversion microscope Leica DM IRB of phase contrast, of fluorescence-coloured nucleus and fluorescence of curcumin, 1—ground curcumin according to Example 1B, 2—native curcumin micronized in composition like tablet 1 according to Example 6, 3—native curcumin micronized with tablet substance according to Example 4A (that means without lecithin and piperine), 4—native curcumin micronized with mannitol, lecithin and piperine, 5—native curcumin micronized with mannitol for cell line MCF-7, human breast carcinoma.
Figure 7:
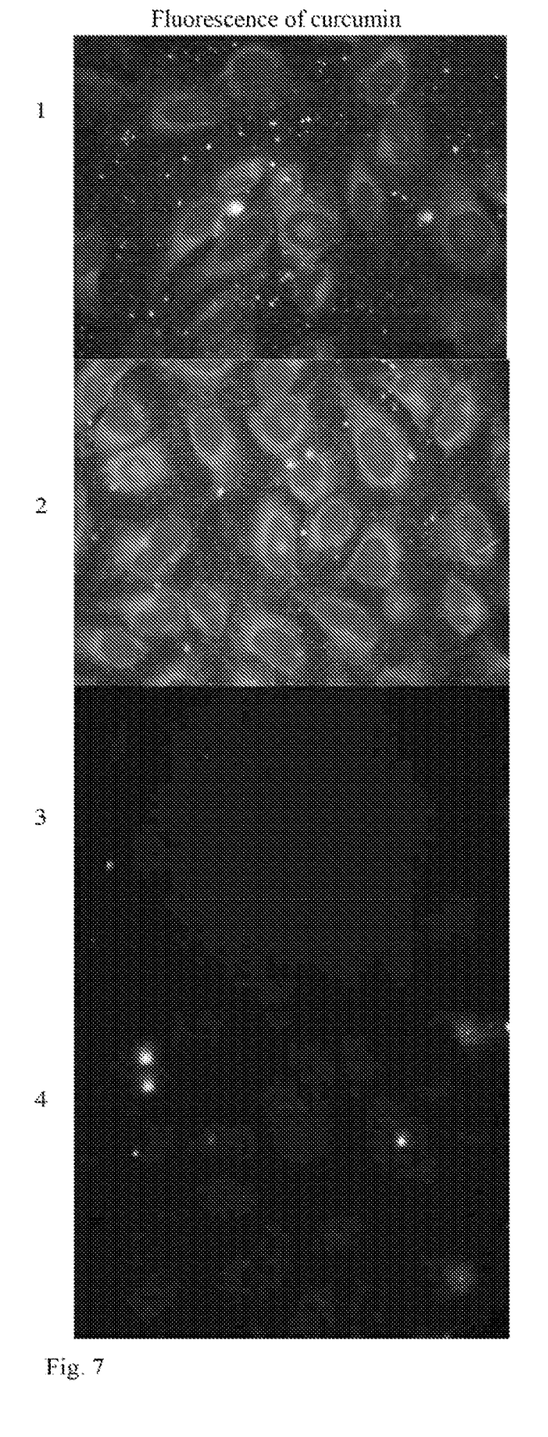
FIG. 7 Snaps by fluorescence inversion microscope Leica DM IRB fluorescence of curcumin, 1—ground curcumin according to Example 1A, 2—ground curcumin according to Example 1B, 3—curcumin of product A, 4—curcumin of product B for cell line U-2, human osteosarcoma.
Figure 8:
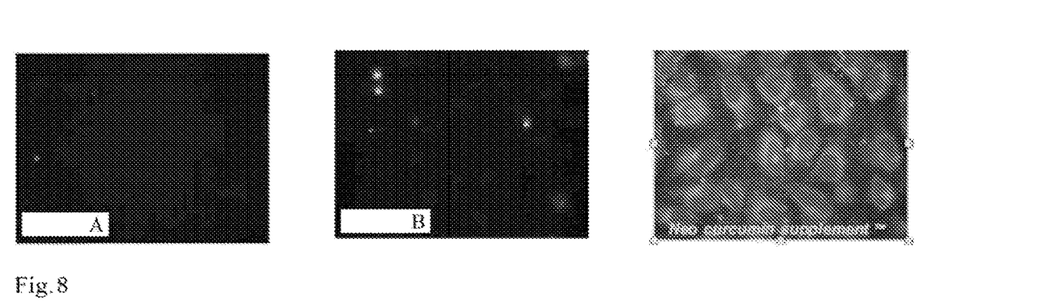
FIG. 8 Snaps by fluorescence inversion microscope Leica DM IRB of phase contrast, of fluorescence-coloured nucleus and fluorescence of ground curcumin according to Example 1B for cell cultures, comparison of formulation of ground curcumin according to this invention with commercial product A and B.
Figure 9:
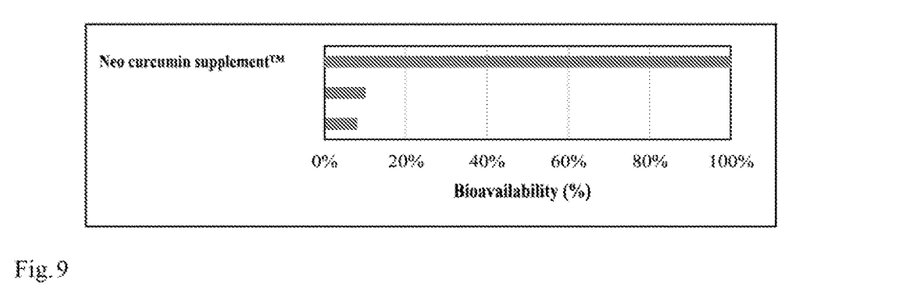
FIG. 9 Graphical representation of bioavailability derived from fluorescence of forms of curcumin from FIG. 8.

Comparison of Bioavailability of an Orodispersible Tablet Containing Highly Bioavailable Curcumin with Commercial Product A and B Tablet 1 prepared according to Example 6 (2 mg of curcumin) and other 2 commercial preparations (2 mg of curcumin) have been resuspended in 1 ml PBS (buffer saline solution), sound treated in a bath for 5 minutes and 40 µl of this suspension has been added to 2 ml of a cultural medium to the cells of human osteosarcoma. Incubation with cells has run in an incubator at 37° C. for 1 hour and then reference dye Hoechst 33342 has been added in the medium for 15 minutes (resulting concentration 0.5 µM) which marks cell nuclei with fluorescence. The cells have been rinsed with the medium without phenol red, they have been viewed using a fluorescence inversion microscope Leica DM IRB using an oil immersion objective (×63) and scanned with a DFC 480 camera. The same cell field has been scanned using common light (phase contrast), and fluorescence cubes Leica A (excitation filter BP340-380 and long pass filter LP 425 for emission) showing blue fluorescence Hoechst 33342 and Leica 13 (excitation filter BP 450-490 and long pass filter LP 515 for emission) showing green fluorescence of curcumin. All the variants of curcumin tested have been scanned with a camera with the same setting to allow their comparison. In vitro experiments have confirmed penetration of the produced nanoformulation with ODT into a cell system much higher than for native curcumin in commercial preparations (FIG. 6).

For formulation of curcumin according to this invention, the real bioavailability has been achieved and this has been derived from comparison of fluorescence intensity of biologically available curcumin according to the invention against commercial native forms of curcumin products A and B.

Example 10

Figure 11:
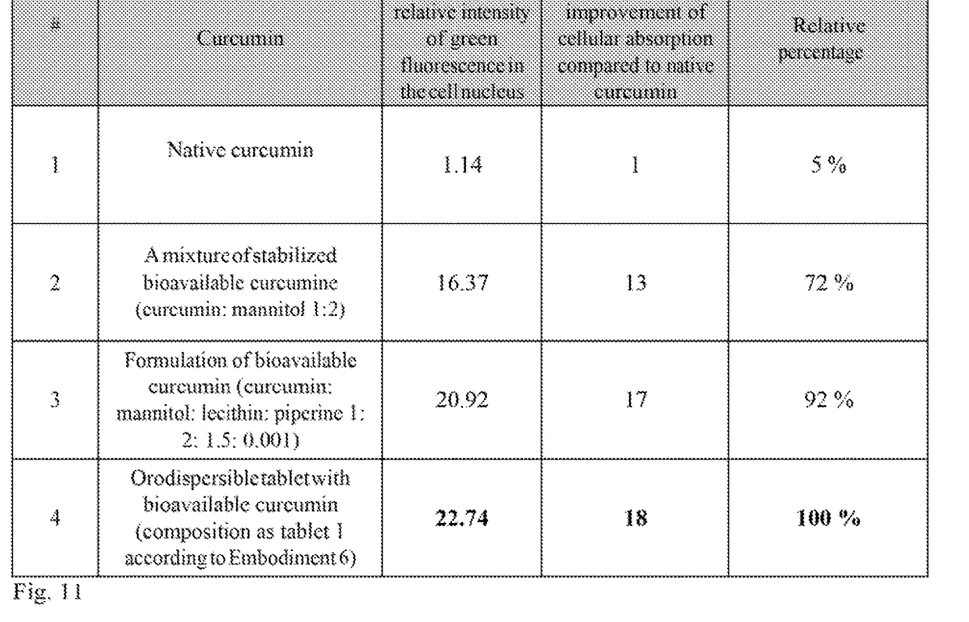
FIG. 11 Table for determination of cell absorption with regard to native curcumin, comparison of fluorescence intensity according to Example 10.
Figure 12:
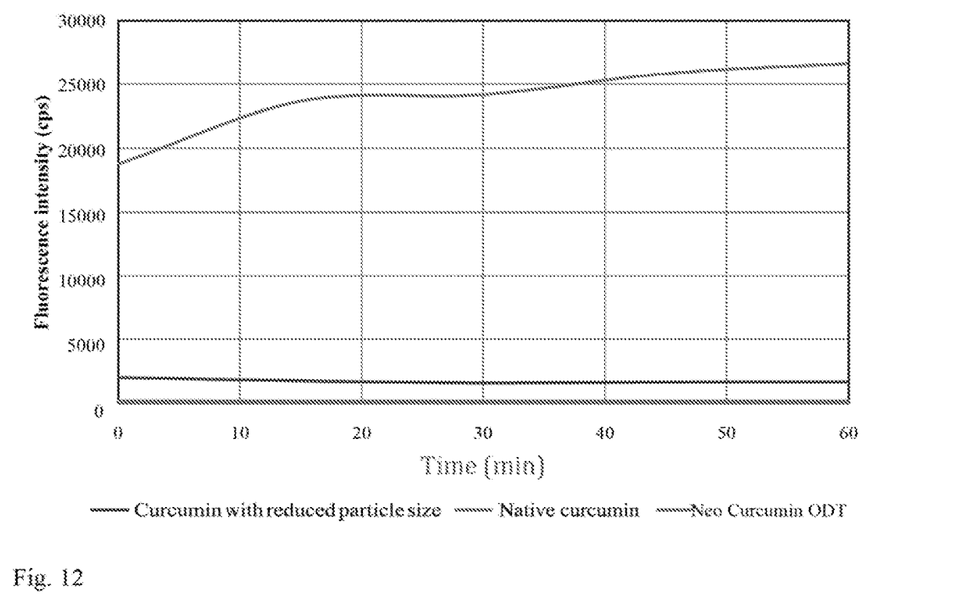
FIG. 12 Plotted dependence of intensity of fluorescence in solution on dilution time. Curcumin with lesser size of particles had curcumin particles with size 2 to 15 μm of product A, ground curcumin according to Example 1B is labelled as Neo Curcumin ODT.
Figure 13:
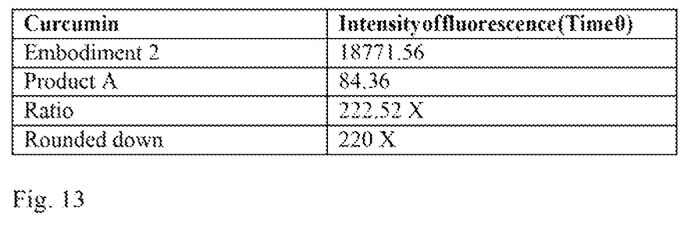
FIG. 13 Table for determination of intensity of fluorescence of diluted curcumin specimens.

Comparison of Bioavailability of an Orodispersible Tablet Containing Highly Bioavailable Curcumin with Native Curcumin, with Native Curcumin Micronized with Mannitol, with Native Curcumin Micronized with Mannitol, Lecithin and Piperine Tablet 1 prepared according to Example 6 (2 mg of curcumin), native curcumin (2 mg), native curcumin micronized with mannitol according to Example 2 (2 mg of curcumin) and native curcumin micronized with mannitol, lecithin and piperine (2 mg of curcumin, 4 mg of mannitol, 3 mg of lecithin, 0.02 mg of piperine) have been resuspended in 1 ml of PBS (buffer saline solution), sound treated in a bath for 5 minutes and 40 μl of this suspension has been added to 2 ml of a cultural medium to the cells of human osteosarcoma. Incubation with cells has run in an incubator at 37° C. for 1 hour and then reference dye Hoechst 33342 has been added in the medium for 15 minutes (resulting concentration 0.5 μM) which marks cell nuclei with fluorescence. The cells have been rinsed with the medium without phenol red, they have been viewed using a fluorescence inversion microscope Leica DM IRB using an oil immersion objective (×63) and scanned with a DFC 480 camera. The same cell field has been scanned using common light (phase contrast), and fluorescence cubes Leica A (excitation filter BP340-380 and long pass filter LP 425 for emission) showing blue fluorescence Hoechst 33342 and Leica 13 (excitation filter BP 450-490 and longpass filter LP 515 for emission) showing green fluorescence of curcumin. All the variants of curcumin tested have been scanned with a camera with the same setting to allow their comparison. In vitro experiments have confirmed penetration of the produced nanoformulation with ODT into a cell system much higher than for native curcumin and other formulations (FIG. 11)

For formulation of curcumin according to this invention, the real bioavailability has been achieved and this has been derived from comparison of fluorescence intensity of biologically available curcumin according to the invention against native curcumin, native curcumin micronized with mannitol and native curcumin micronized with manitol, lecithin and piperine.

APPLICATION IN INDUSTRY

Food additive in form of tablets free soluble in mouth, containing highly absorbable curcumin

The invention claimed is:

1. An orodispersible oral soluble tablet with biologically available curcumin that is stabilized to a particle size of 100 to 250 nm, by preventing reverse aggregation of the curcumin particles by forming a curcumin-mannitol cluster, and thereby increasing biological availability and cell penetration of curcumin, the tablet comprising a mixture of a curcumin-mannitol cluster and an orodispersible oral soluble carrier, where the curcumin-mannitol cluster is a combination of curcumin and mannitol in weight ratio 1:1 to 3 grounded together to the particle size 100 to 250 nm, where the curcumin comprises particles of extract of rhizome of plant *Curcuma longa* containing at least 95% by weight of curcumin, and the orodispersible oral soluble carrier comprising 20 to 80% by weight of tapioca starch, 10 to 30% by weight of pulverized bamboo fiber and 1 to 20% by weight of acid hydrolysed dextrin, wherein the biologically available curcumin is in lipid in a weight ratio 0.35 to 1.5:1 of lipid against curcumin with presence of piperine in a weight ratio 0.0025 to 0.1:1 of piperine against curcumin, and wherein the lipid is lecithin.

2. The orodispersible oral soluble tablet with biologically available curcumin according to claim 1, wherein the weight ratio of curcumin against mannitol is 1:2.

3. The orodispersible oral soluble tablet with biologically available curcumin according to claim 1, wherein the particle size of curcumin extract is 110 to 180 nm.

4. The orodispersible oral soluble tablet with biologically available curcumin according to claim 1, wherein the orodispersible oral soluble carrier is comprising 0.05 to 10% by weight Stevio-Rebauoside A.

5. The orodispersible oral soluble tablet with biologically available curcumin according to claim 1, wherein the orodispersible oral soluble carrier is comprising 1 to 10% by weight of isomalt.

6. The orodispersible oral soluble tablet with biologically available curcumin according to claim 1 it is comprising up to 97% by weight of the orodispersible carrier.

7. The orodispersible oral soluble tablet with biologically available curcumin according to claim 1, wherein the orodispersible oral soluble carrier is comprising 10 to 50% by weight of erythritol or sorbitol or xylitol or their mixture.

8. The orodispersible oral soluble tablet with biologically available curcumin according to claim 1, wherein the orodispersible oral soluble carrier is comprising 1 to 8% by weight of sliding substances.

9. The orodispersible oral soluble tablet with biologically available curcumin according to claim 1 comprising sliding substances, which are 0.5 to 4% by weight of silicon dioxide and 0.4 to 4% by weight of glycerol dibehenate and 0.01 to 10% by weight of pre-gelatinised starch.

10. The orodispersible oral soluble tablet with biologically available curcumin according to claim 8, wherein the sliding substances are stearate magnesium, stearate aluminum, sodium lauryl sulphate, talc, polyethylene glycol, stearic acid, boric acid or their mixture.

11. The orodispersible oral soluble tablet with biologically available curcumin according to claim 1, wherein the orodispersible oral soluble carrier is comprising 0.01 to 10% by weight of aroma or flavour.

* * * * *